Figure 1:
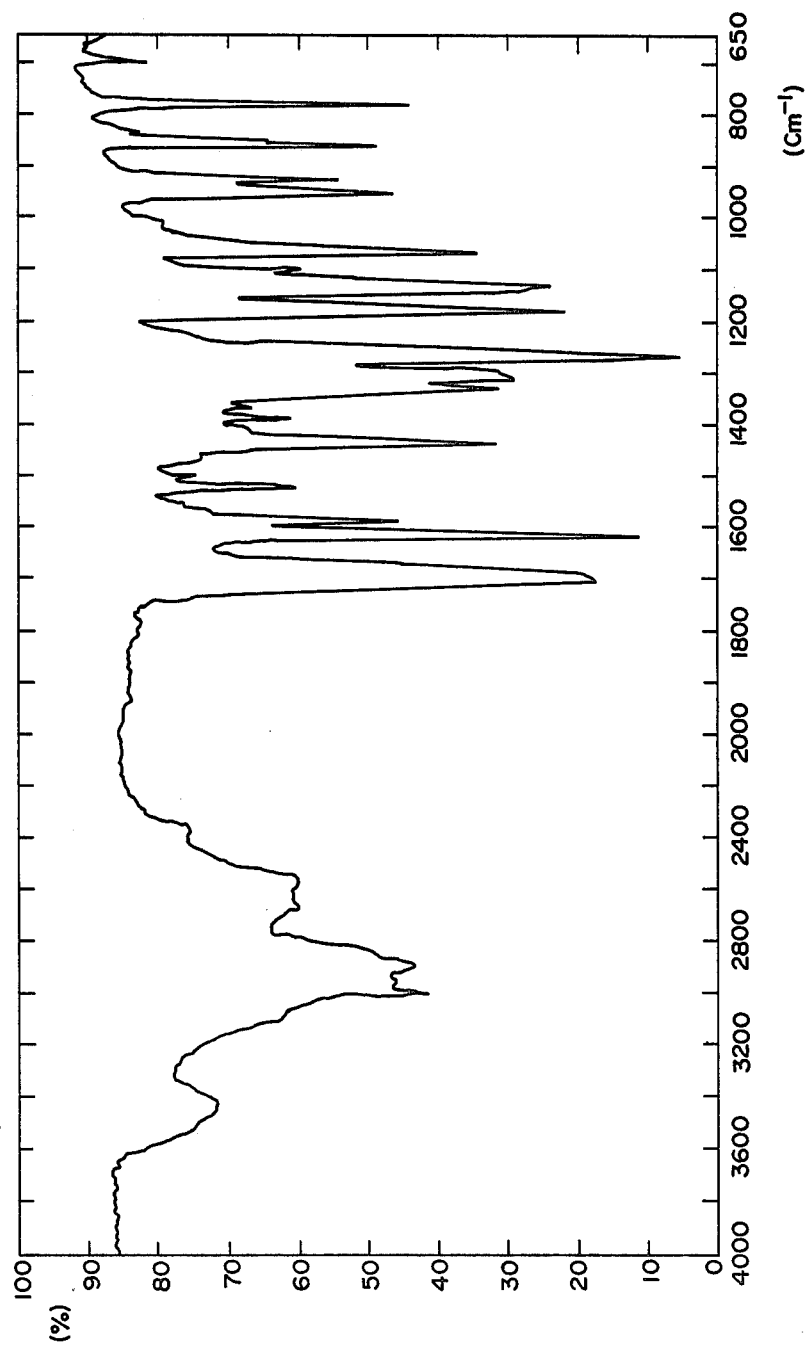

United States Patent [19]
Inukai et al.

[11] 4,158,011
[45] Jun. 12, 1979

[54] p'-CYANOPHENYL ESTER OF p-(β-ALKOXY)ETHOXYBENZOIC ACID

[75] Inventors: Takashi Inukai; Hideo Sato, both of Yokohama, Japan

[73] Assignee: Chisso Corporation, Osaka, Japan

[21] Appl. No.: 849,737

[22] Filed: Nov. 9, 1977

[30] Foreign Application Priority Data
Nov. 26, 1976 [JP] Japan .................... 51/141917

[51] Int. Cl.² .................... C07C 121/75
[52] U.S. Cl. .................... 260/465 D; 252/299; 350/350; 562/473
[58] Field of Search .................... 260/465 D; 252/299

[56] References Cited
U.S. PATENT DOCUMENTS
3,923,857 12/1975 Boller et al. .................... 260/465 D Primary Examiner—Dolph H. Torrence
Attorney, Agent, or Firm—Fred Philpitt

[57] ABSTRACT

A compound which is useful as one component of liquid crystal composition having superior practical properties and positive dielectric anisotropy is provided. Said compound is p'-cyanophenyl ester of p-(β-alkoxy)ethoxybenzoic acid represented by the general formula

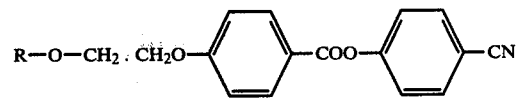

wherein R is a straight chain alkyl group having 1 – 6 carbon atoms.

2 Claims, 4 Drawing Figures

FIG. I

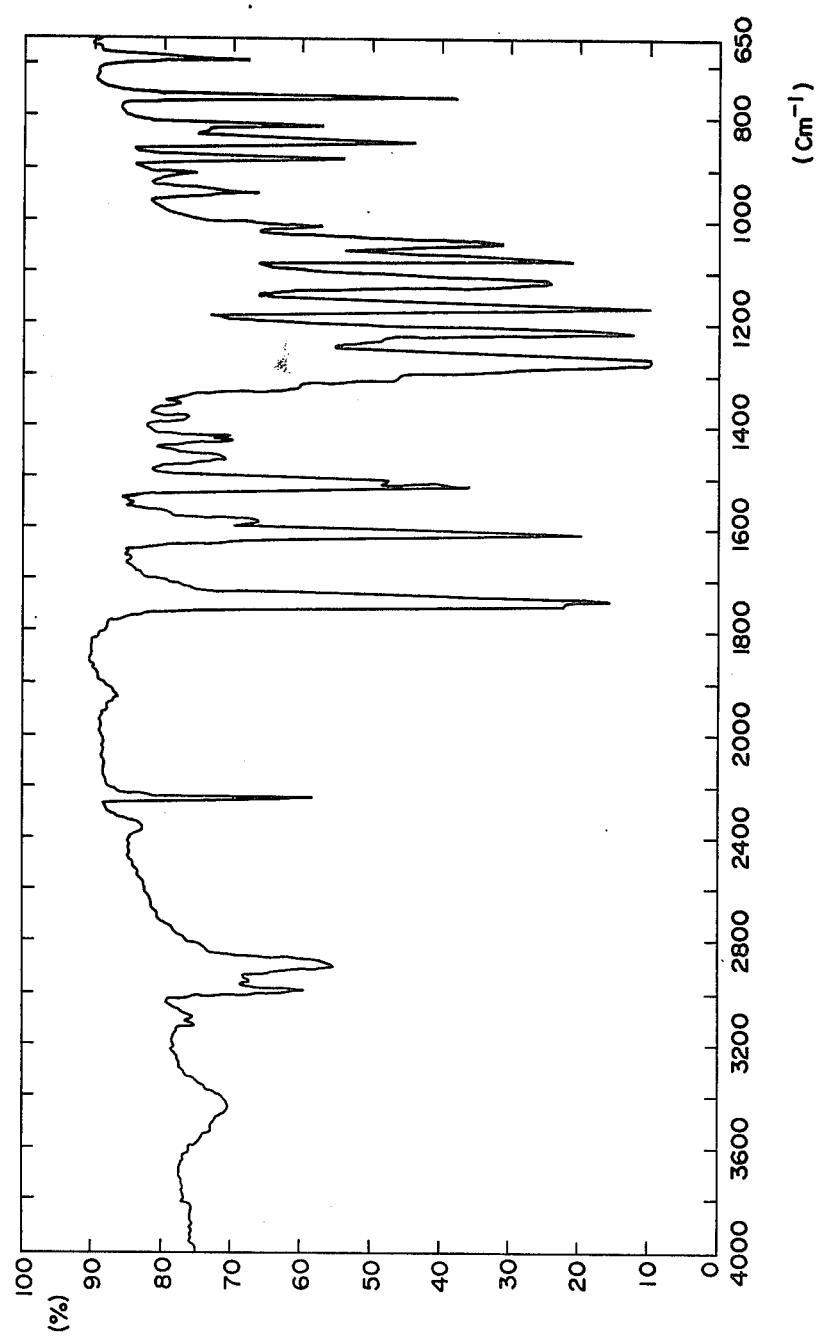
F I G. 2 p'-CYANOPHENYL ESTER OF p-(β-ALKOXY)ETHOXYBENZOIC ACID

DESCRIPTION OF THE INVENTION

This invention relates to a novel organic compound. More particularly it relates to a novel organic compound capable of being used as one component of liquid crystal material having a positive dielectric anisotropy.

As is well known, liquid crystal materials having a dielectric anisotropy can be used not only for display elements which use a nematic liquid crystal having a twisted liquid crystal arrangement (so-called twisted nematic cell), but also for liquid crystal display elements which use liquid crystals containing a suitable coloring material and in which a guest-host effect is applied, and for other purposes. If these liquid crystal materials are used in the form of a single compound, they are not fit for practical uses in the points of their performances i.e. temperature range of liquid crystal, threshhold voltage, response velocity, stability, etc. It is the present status that those which are fit for a certain extent of usage are obtained in practice by mixing several kinds of liquid crystal compounds or non-liquid-crystal compounds.

It is an object of this invention to provide a compound which is useful as one component which constitutes a liquid crystal composition having superior practical performances and a positive dielectric anisotropy.

When a compound of the present invention is added to a liquid crystal having a negative dielectric anisotropy, there can be formed a liquid crystal composition having a positive dielectric anisotropy. When this compound is added to a liquid crystal having a positive dielectric anisotropy, it is possible to make its threshhold voltage lower.

The compound of the present invention is p'-cyanophenyl ester of p-(β-alkoxy) ethoxybenzoic acid having the general formula

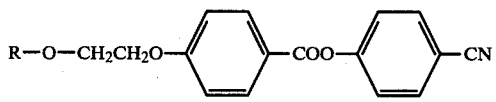

(I)

wherein R represents a straight chain alkyl group having 1–6 carbon atoms. This compound, by itself, does not exhibit a liquid crystal state or at least does not exhibit an enantropic liquid state, but it is possible to obtain liquid crystal compositions having superior performances, by adding this compound to other liquid crystal materials. Although the compound of the present invention is a material which by itself hardly exhibits a liquid crystal state, but in case this material is added to other liquid crystal material, it behaves as if it were by itself a superior liquid crystal material having a positive dielectric anisotropy. For example, liquid crystal compounds of the class of 4-alkoxy-4'-alkylbenzene exhibit a negative dielectric anisotropy and cannot be used by themselves alone for twisted nematic type liquid crystal cells, but when a compound of this invention is added thereto, it is possible to obtain a nematic liquid crystal having a positive dielectric anisotropy. Further, when a compound of the present invention is added to a liquid crystal composition of the classes of cyanobiphenyl and cyanoterphenyl having a positive dielectric anisotropy, it is possible to obtain a liquid crystal composition having lower threshhold voltage and saturation voltage. It goes without saying that such a lowering of threshhold voltage is advantageous for actuating liquid crystal display elements.

It is possible to obtain the compound (I) of the present invention according to the following procedure:

Firstly, p-(β-alkoxy)ethoxybenzoic acid (II) having the general formula

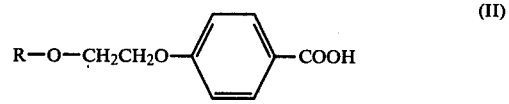

(II)

wherein R represents the same alkyl as that of the formula (I), is produced by reacting p-hydroxybenzoic acid with a β-alkoxyethyl bromide in an alcohol in the presence of potassium hydroxide, or by reacting an alkali metal salt of p-hydroxybenzoic acid ester with a β-alkoxyethyl bromide in a solvent such as dimethylformamide or the like. The resulting p-(β-alkoxy)ethoxybenzoic acid is reacted with thionyl chloride to give its acid chloride, which is then reacted with p-cyanophenol in a solvent such as benzene, pyridine or the like, followed by separation and purification, to obtain an objective substance.

The present invention will be further illustrated by way of the specific examples which follow hereinafter.

The melting points of the compounds (I) thus obtained, of the present invention and the melting points of the compounds (II) as the intermediate compounds thereof are shown in the following Table.

Table

| R | Melting points °C. | | |
|---|---|---|---|
| | Compound (I) | Compound (II) | |
| $CH_3$ | 107.9–108.2*[1] | 152–152.4 | |
| $C_2H_5$ | 64.7–65.8 | 130–132 | Example 1 |
| $n-C_3H_7$ | 44.8–46.0 | 116–117 | |
| $n-C_4H_9$ | 43–44, 50–51*[2] | 114.5–115 | Example 2 |
| $n-C_5H_{11}$ | 41.8–42.3 | 104–104.5 | |
| $n-C_6H_{13}$ | 37.5–38.0 | 100–101 | |

*[1] Monotropic liquid crystal (N-I point (clear point) 68°–69° C.
*[2] It has two crystalline forms having different melting points.

Compounds having an R of more than 6 carbon atoms exhibit too low melting points, and in case a liquid crystal composition containing such compounds is used as a display element, the latter comes to exhibit a function of retarding the response velocity and is not suitable to the object of the present invention. Most preferable compounds are those in which R is $n-C_3H_7$ or $n-C_4H_9$. It is relatively difficult to use the compound in which R is $CH_3$ because of relatively high melting point.

In order to describe more fully the present invention, examples of the preparation of the compounds of the present invention and examples of the cases of application where these compounds are added to other liquid crystal compounds.

EXAMPLE 1

(1) Preparation of p-(β-ethoxy)ethoxybenzoic acid

Into a 1 l three-neck flask were introduced 400 ml of 90% ethanol, 25 g of potassium hydroxide, 40 g of p-hydroxybenzoic acid and 45 g of β-ethoxyethyl bromide, and the contents were heated under reflux for 10 hours. After removing ethanol by distillation, 100 ml of a 10% aqueous solution of potassium hydroxide was added and the contents were heated under reflux for additional two hours. After acidifying with hydrochloric acid, separated acid was collected and recrystallized from benzene and then ethanol to obtain 18 g of p-($\beta$-ethoxy)ethoxybenzoic acid. The melting point of the resulting product was 130° C.–132° C. and the elemental analysis values thereof were as follows, which accorded with the calculated values very well.

|   | Analytic values | Calculated values (as $C_7H_{14}O_4$) |
|---|---|---|
| C | 62.7% | 62.84% |
| H | 6.6% | 6.71% |

The infrared absorption spectra of the resultant product are shown in FIG. 1.

(2) Preparation of p'-cyanophenyl ester of p-($\beta$-ethoxy)ethoxybenzoic acid (a compound of the formula (I) in which R is $C_2H_5$)

To 14 g of p-($\beta$-ethoxy)ethoxybenzoic acid obtained in the above-mentioned section (1) was added about 15 g of thionyl chloride, and after heating under reflux for 30 minutes, excessive thionyl chloride was distilled off. To the resulting product, a solution consisting of 9 g of p-cyanophenol, 20 ml of pyridine and 100 ml of benzene were added, and after heating under reflux for one hour, the product was cooled with water and poured on ice. After successive washings with diluted hydrochloric acid, a diluted aqueous solution of sodium hydroxide and water, benzene was distilled off. Remaining solid matters were recrystallized from water-containing methanol to obtain 12 g of p'-cyanophenyl ester of p-($\beta$-ethoxy)ethoxybenzoic acid. The melting point of this material was 64.7°–65.8° C. and the values of the elemental analysis showed a good agreement with the calculated values as shown below.

|   | Analytic value | Calculated value (as $C_{18}H_{17}O_4N_1$) |
|---|---|---|
| C | 69.4% | 69.44% |
| H | 5.6% | 5.51% |
| N | 4.4% | 4.50% |

Further the infrared absorption spectra of this material are shown in FIG. 2.

EXAMPLE 2

(1) Preparation of p-($\beta$-n-butoxy)ethoxybenzoic acid

To a 1 l three-neck flask were added 70 g of sodium salt of p-hydroxybenzoic acid

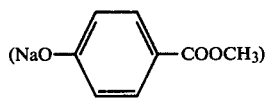

and 200 ml of N,N-dimethylformamide, and the contents were heated under reflux. To the heated contents, 50 g of $\beta$-n-butoxyethyl bromide was dropped over a period of 30 minutes and heating was continued under reflux for further 8 hours. After cooling with water, 300 ml of water and 200 ml of toluene were added to the contents and after shaking, the resulting organic layer was separated, washed with 4 N hydrochloric acid and then with a 20% aqueous solution of sodium hydroxide. After distilling off toluene and heating the remaing material together with 200 ml of a 20% aqueous solution of sodium hydroxide for 3 hours, the resulting material was neutralized with hydrochloric acid to precipitate the objective material. After washing with water, the objective material was recrystallized from ethanol to obtain 55 g of p-($\beta$-n-butoxy)ethoxybenzoic acid. The melting point of this material was 114.5°–115° C. and the values of the elemental analysis thereof showed a good agreement with the calculated values as seen below.

|   | Analytical value | Calculated value (as $C_{13}H_{18}O_4$) |
|---|---|---|
| C | 65.5% | 65.53% |
| H | 7.6% | 7.61% |

Figure 3:
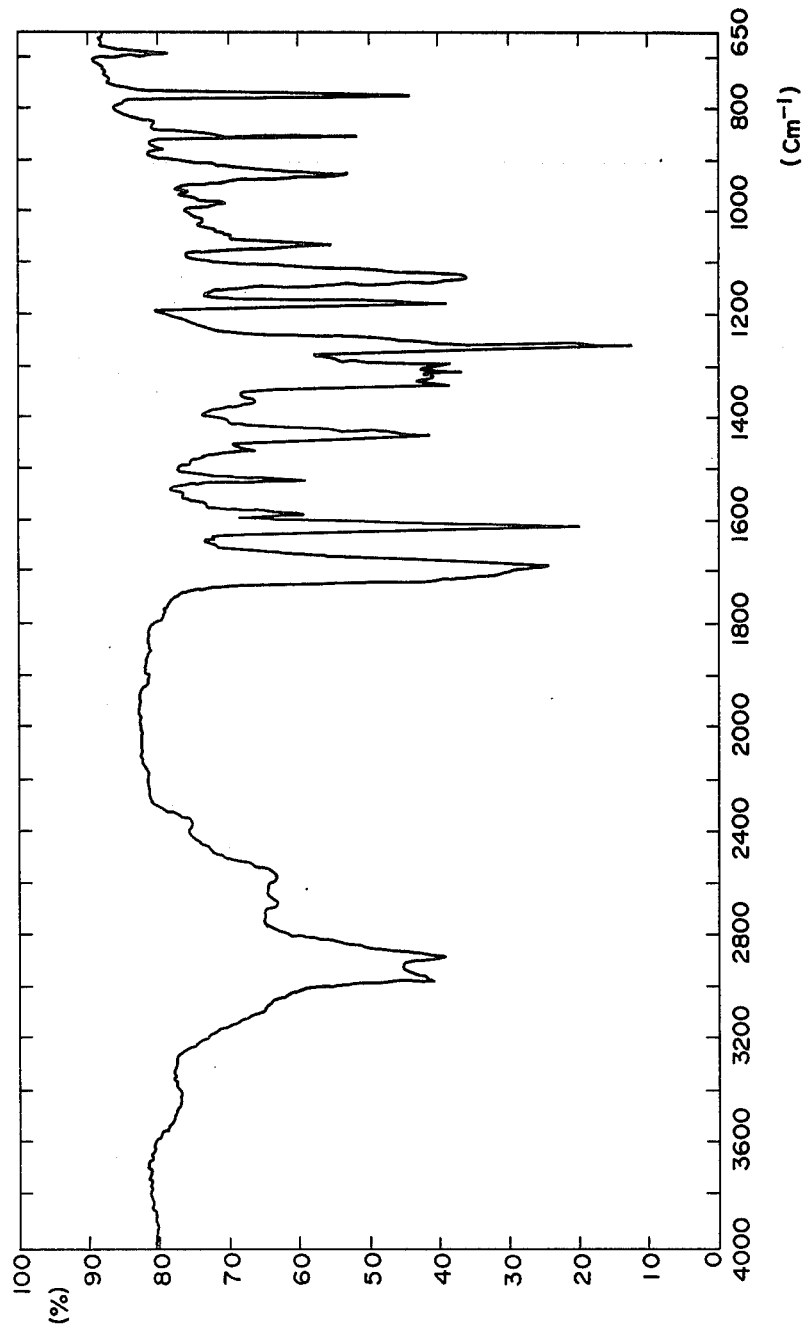

Further the infrared absorption spectra are shown in FIG. 3.

(2) Preparation of p'-cyanophenyl ester of p-($\beta$-butoxy)ethoxybenzoic acid (R=n-$C_4H_9$ in the formula (1))

By using the p-($\beta$-butoxy)ethoxybenzoic acid obtained in the above-mentioned section (1) and according to the same method as that of (2) of Example 1, p'-cyanophenyl ester of p-($\beta$-butoxy)ethoxybenzoic acid was obtained. This material showed two crystalline forms having a melting point of 43°–44° C. and a melting point of 50°–51° C., respectively, and the values of elemental analysis showed good agreement with the calculated values thereof as shown below.

|   | Analytical value | Calculated value (as $C_{28}H_{21}O_4N_1$) |
|---|---|---|
| C | 70.7% | 70.78% |
| H | 6.3% | 6.24% |
| N | 4.2% | 4.13% |

Figure 4:
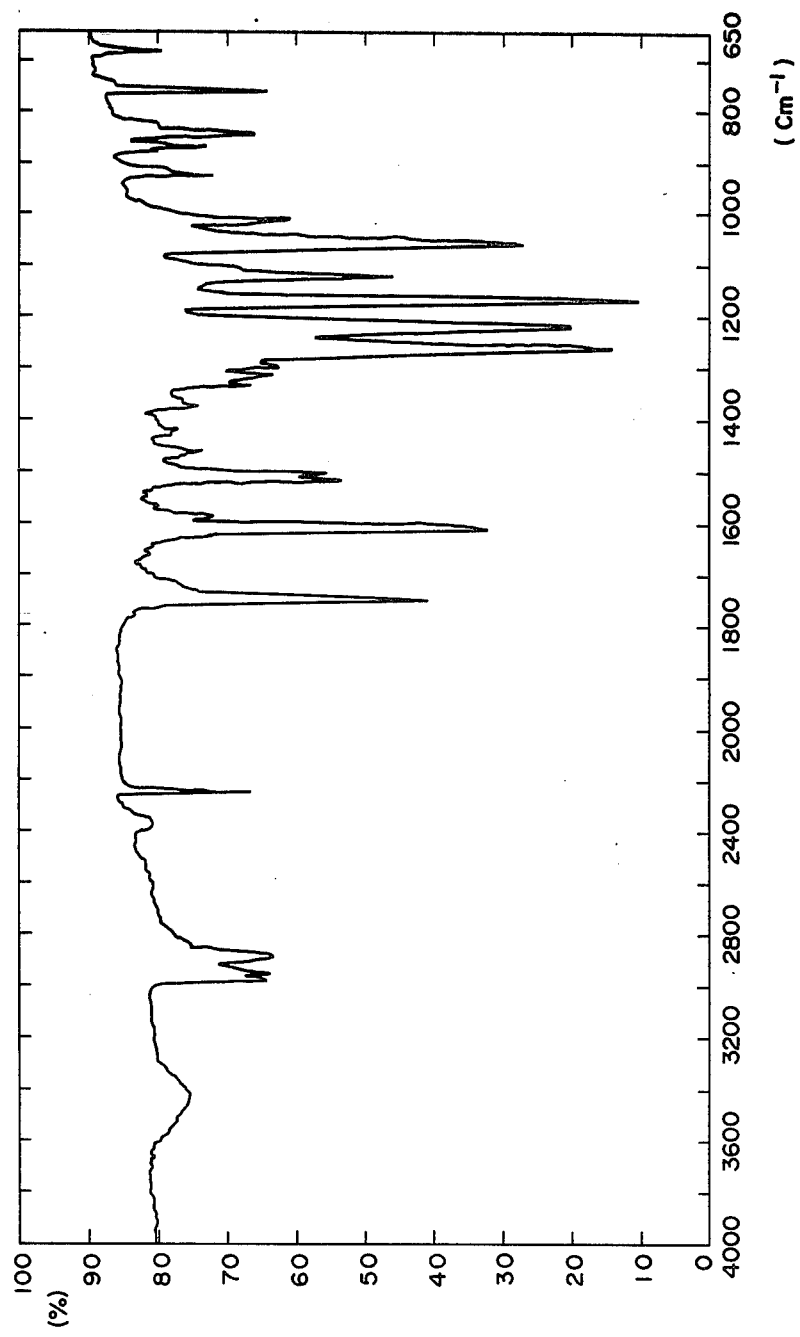

The infrared absorption spectra of this material are shown in FIG. 4.

EXAMPLE 3 (Application example 1)

A mixture of 35 g of 4-methoxy-4'-ethylazoxybenzene and 65 g of 4-methoxy-4'-n-butylazoxybenzene is a liquid crystal having a negative dielectric anisotropy and it cannot be utilized by itself for a liquid crystal cell of twisted nematic type. A mixed liquid crystal prepared by adding 10 g of p'-cyanophenyl ester of p-($\beta$-ethoxy)ethoxybenzoic acid obtained in Example 1 to the above-mentioned mixture is a nematic liquid crystal having an upper limit of nematic temperature range of 66.3° C. and a positive dielectric anisotropy. When it is used for a twisted nematic type liquid crystal cell, as for the resulting electro-optical effectivenesses, its threshold voltage was 2.5 V and its saturation voltage was 3.7 V (the temperature of measurement was 25° C., in this example as well as in all the following examples).

EXAMPLE 4 (Example of Application 2)

A liquid crystal mixture obtained by using p'-cyanophenyl ester of p-($\beta$-n-butoxy)ethoxybenzoic acid in place of p'-cyanophenyl ester of p-($\beta$-ethoxy)ethoxybenzoic acid used in the foregoing example 3 was a nematic liquid crystal having an upper limit of nematic temperature range of 65.0° C. and a positive dielectric anisotropy. When it was used in a twisted namatic type liquid crystal cell, the characteristic properties as the electro-optical effectivenesses were same as those in Example 3.

EXAMPLE 5 (Example of Application 3)

A liquid crystal consisting of 32 g of 4-n-pentyl-4'-cyanobiphenyl, 20 g of 4-n-heptyl-4'-cyanobiphenyl, 11 g of 4-n-octyloxy-4'-cyanobiphenyl and 7 g of 4-n-pentyl-4'-cyanoterphenyl has a positive dielectric anisotropy, and when it is used for a twisted nematic type liquid crystal cell, as for the electro-optical effectivenesses, its threshhold voltage is 1.4 V and its saturation voltage is 2.1 V, but a liquid crystal mixture obtained by adding, to 70 g of the above-mentioned liquid crystal mixture, 15 g of p'-cyanophenyl ester of p-($\beta$-ethoxy)ethoxybenzoic acid and 15 g of p'-cyanophenyl ester of p-($\beta$-n-butoxy)ethoxybenzoic acid had an upper limit of nematic temperature range of 50.2° C. When it was used for a twisted nematic type liquid crystal cell, as for the electro-optical effectivenesses, its threshhold voltage was reduced to 1.1 V and its saturation voltage was reduced to 1.7 V.

In the accompanying drawings,

FIG. 1 shows infrared absorption spectra of p-($\beta$-ethoxy)ethoxybenzoic acid obtained according to Example 1 (1); FIG. 2 shows infrared absorption spectra of p'-cyanophenyl ester of p-($\beta$-ethoxy)ethoxybenzoic acid obtained according to Example 1 (2); FIG. 3 shows infrared absorption spectra of p-($\beta$-n-butoxy)ethoxybenzoic acid obtained according to Example 2 (1); and FIG. 4 shows infrared absorption spectra of p'-cyanophenyl ester of p-($\beta$-n-butoxy)ethoxybenzoic acid.

What is claimed is:

1. p'-Cyanophenyl esters of p-($\beta$-alkoxy)ethoxybenzoic acid represented by the general formula

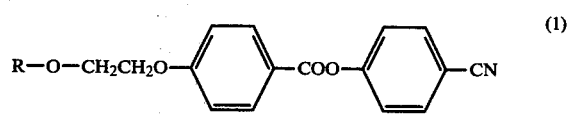

(1)

wherein R represents a straight chain alkyl group having 1–6 carbon atoms.

2. A compound according to claim 1 wherein R of the formula (I) is n-$C_3H_7$ or n-$C_4H_9$.

* * * * *